(12) United States Patent
Mendel et al.

(10) Patent No.: US 6,376,552 B1
(45) Date of Patent: Apr. 23, 2002

(54) TREATMENT OF GALLSTONES

(75) Inventors: Carl M. Mendel, Short Hills; Timothy B. Seaton, Far Hills, both of NJ (US); Steve P. Weinstein, Hartsdale, NY (US)

(73) Assignee: Knoll Pharmaceutical Company, Mount Olive, NJ (US)

( * ) Notice: Subject to any disclaimer, the term of this patent is extended or adjusted under 35 U.S.C. 154(b) by 0 days.

(21) Appl. No.: 09/527,962

(22) Filed: Mar. 17, 2000

Related U.S. Application Data

(60) Provisional application No. 60/125,340, filed on Mar. 19, 1999, now abandoned.

(51) Int. Cl.$^7$ ............................................... A61K 31/22
(52) U.S. Cl. ...................................................... 514/646
(58) Field of Search ......................................... 514/646

(56) References Cited

U.S. PATENT DOCUMENTS 5,459,164 A * 10/1995 Vargas ........................ 514/646

FOREIGN PATENT DOCUMENTS

WO      WO 95/20949 A1      8/1995

\* cited by examiner

*Primary Examiner*—Rebecca Cook
(74) *Attorney, Agent, or Firm*—John D. Conway

(57) ABSTRACT

A compound of formula I

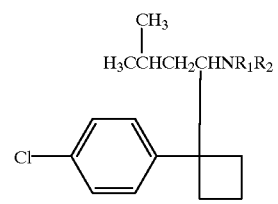

or a pharmaceutically acceptable salt thereof in which $R_1$ and $R_2$ are independently H or methyl (for example N,N-dimethyl-1-[1-(4-chlorophenyl)cyclobutyl]-3-methylbutyl amine hydrochloride optionally in the form of its monohydrate) is used for treating gallstones, particularly gallstones associated with weight loss or associated with gall bladder disease related to obesity.

13 Claims, No Drawings

TREATMENT OF GALLSTONES

CROSS REFERENCE TO RELATED APPLICATION

This application claims the benefit of U.S. Provisional Application No. 60/125,340, filed Mar. 19, 1999, now abandoned.

This invention relates to a method of treating gallstones.

According to the present invention there is provided a method of treating gallstones, in which a therapeutically effective amount of a compound of formula I

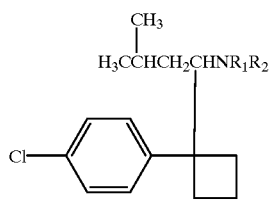

including enantiomers and pharmaceutically acceptable salts thereof, in which $R_1$ and $R_2$ are independently H or methyl, is administered in conjunction with a pharmaceutically acceptable diluent or carrier to a human in need thereof.

The occurrences of gallstones which may advantageously be treated with a compound of formula I include gallstones associated with obesity and gallstones which are associated with weight loss.

A preferred compound of formula I is N,N-dimethyl-1-[1-(4-chlorophenyl)cyclobutyl]-3-methylbutylamine or a salt thereof, for example the hydrochloride salt. A preferred form of this hydrochloride is its monohydrate.

The preparation and use of compounds of formula I, such as N,N-dimethyl-1-[1-(4-chlorophenyl)cyclobutyl]-3-methylbutylamine, N-{1-[1-(4-chlorophenyl)-cyclobutyl]-3-methylbutyl}-N-methylamine, and 1-[1-(4-chlorophenyl)-cyclobutyl]-3-methylbutylamine and salts thereof, in the treatment of depression is described in British Patent Specification 2098602 and U.S. Pat. No. 4,522,828. The use of compounds of formula I such as N,N-dimethyl-1-[1-(4-chlorophenyl)cyclobutyl]-3-methylbutylamine and salts thereof in the treatment of Parkinson's disease is described in published PCT application WO 88/06444. The use of N,N-dimethyl-1-[1-(4-chlorophenyl)cyclobutyl]-3-methylbutylamine and salts thereof in the treatment of cerebral function disorders is described in U.S. Pat. No. 4,939,175. The use of N,N-dimethyl-1-[1-(4-chlorophenyl)cyclobutyl]-3-methylbutylamine hydrochloride in the treatment of obesity is described in published PCT application WO 90/06110. A particularly preferred form of this compound is N,N-dimethyl-1-[1-(4-chlorophenyl)cyclobutyl]-3-methylbutylamine hydrochloride monohydrate (sibutramine hydrochloride) which is described in European Patent Number 230742. The use of N,N-dimethyl-1-[1-(4-chlorophenyl) cyclobutyl]-3-methylbutylamine and salts thereof for improving the glucose tolerance of humans having Impaired Glucose Tolerance or Non-insulin Dependent Diabetes Mellitus is described in published PCT application WO 95/20949.

It will be appreciated by those skilled in the art that compounds of formula I contain a chiral centre. When a compound of formula I contains a single chiral centre it may exist in two enantiomeric forms. The present invention includes the use of the individual enantiomers and mixtures of the enantiomers. The enantiomers may be resolved by methods known to those skilled in the art, for example by formation of diastereoisomeric salts or complexes which may be separated, for example, by crystallisation; via formation of diastereoisomeric derivatives which may be separated, for example, by crystallisation, gas-liquid or liquid chromatography; selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, for example silica with a bound chiral ligand or in the presence of a chiral solvent. It will be appreciated that where the desired enantiomer is converted into another chemical entity by one of the separation procedures described above, a further step is required to liberate the desired enantiomeric form. Alternatively, specific enantiomers may be synthesised by asymmetric synthesis using optically active reagents, substrates, catalysts or solvents, or by converting one enantiomer to the other by asymmetric transformation.

Preferred compounds of formula I are N,N-dimethyl-1-[1-(4-chlorophenyl)-cyclobutyl]-3-methylbutylamine, N-{1-[1-(4-chlorophenyl)cyclobutyl]-3-methylbutyl}-N-methylamine, and 1-[1-(4-chlorophenyl)cyclobutyl]-3-methylbutylamine including racemates, individual enantiomers and mixtures thereof, and pharmaceutically acceptable salts thereof.

The individual enantiomers can be prepared by enantioselective synthesis from optically active precursors, or by resolving the racemic compound which can be prepared as described above. Enantiomers of secondary amines of the formula I can also be prepared by preparing the racemate of the corresponding primary amine, resolving the latter into the individual enantiomers, and then converting the optically pure primary amine enantiomer into the required secondary amine by methods described in British Patent Specification 2098602.

Specific examples of compounds of formula I are:

(+)-N-[1-[1-(4-chlorophenyl)cyclobutyl]-3-methylbutyl}-N-methylamine;

(−)-N-{1-[1-(4-chlorophenyl)cyclobutyl-3-methylbutyl}-N-methylamine;

(+)-1-[1-(4-chlorophenyl)cyclobutyl]-3-methylbutylamine;

(−)-1-[1-(4-chlorophenyl)cyclobutyl]-3-methylbutylamine;

(+)-N-{1-[1-(4-chlorophenyl)cyclobutyl]-3-methylbutyl}-N-N-dimethylamine;

(−)-N-{1-[1-(4-chlorophenyl)cyclobutyl]-3-methylbutyl}-N-N-dimethylamine.

The hydrochloride salts are preferred in each case, but the free bases and other pharmaceutically acceptable salts are also suitable.

The compound of formula I may be administered in any of the known pharmaceutical dosage forms. The amount of the compound to be administered will depend on a number of factors including the age of the patient, the severity of the condition and the past medical history of the patient and always lies within the sound discretion of the administering physician but it is generally envisaged that the dosage of the compound to be administered will be in the range 0.1 to 50 mg preferably 1 to 30 mg per day given in one or more doses.

Oral dosage forms are the preferred compositions for use in the present invention and these are the known pharmaceutical forms for such administration, for example tablets, capsules, granules, syrups and aqueous or oil suspensions. The excipients used in the preparation of these compositions are the excipients known in the pharmacist's art. Tablets may be prepared from a mixture of the active compound with fillers, for example calcium phosphate; disintegrating agents, for example maize starch; lubricating agents, for example magnesium stearate; binders, for example microcrystalline cellulose or polyvinylpyrrolidone and other optional ingredients known in the art to permit tableting the mixture by known methods. The tablets may, if desired, be coated using known methods and excipients which may include enteric coating using for example hydroxypropylmethylcellulose phthalate. The tablets may be formulated in a manner known to those skilled in the art so as to give a sustained release of the compounds of the present invention. Such tablets may, if desired, be provided with enteric coatings by known methods, for example by the use of cellulose acetate phthalate. Similarly, capsules, for example hard or soft gelatin capsules, containing the active compound with or without added excipients, may be prepared by known methods and, if desired, provided with enteric coatings in a known manner. The contents of the capsule may be formulated using known methods so as to give sustained release of the active compound. The tablets and capsules may conveniently each contain 1 to 50 mg of the active compound.

Other dosage forms for oral administration include, for example, aqueous suspensions containing the active compound in an aqueous medium in the presence of a non-toxic suspending agent such as sodium carboxy-methylcellulose, and oily suspensions containing a compound of the present invention in a suitable vegetable oil, for example arachis oil. The active compound may be formulated into granules with or without additional excipients. The granules may be ingested directly by the patient or they may be added to a suitable liquid carrier (for example, water) before ingestion. The granules may contain disintegrants, e.g. an effervescent couple formed from an acid and a carbonate or bicarbonate salt to facilitate dispersion in the liquid medium.

The therapeutically active compounds of formula I may be formulated into a composition which the patient retains in his mouth so that the active compound is administered through the mucosa of the mouth.

Dosage forms suitable for rectal administration are the known pharmaceutical forms for such administration, for example, suppositories with cocoa butter or polyethylene glycol bases.

Dosage forms suitable for parenteral administration are the known pharmaceutical forms for such administration, for example sterile suspensions or sterile solutions in a suitable solvent.

Dosage forms for topical administration may comprise a matrix in which the pharmacologically active compounds of the present invention are dispersed so that the compounds are held in contact with the skin in order to administer the compounds transdermally. A suitable transdermal composition may be prepared by mixing the pharmaceutically active compound with a topical vehicle, such as a mineral oil, petrolatum and/or a wax, e.g. paraffin wax or beeswax, together with a potential transdermal accelerant such as dimethyl sulphoxide or propylene glycol. Alternatively the active compounds may be dispersed in a pharmaceutically acceptable cream, gel or ointment base. The amount of active compound contained in a topical formulation should be such that a therapeutically effective amount of the compound is delivered during the period of time for which the topical formulation is intended to be on the skin.

The therapeutically active compound of formula I may be formulated into a composition which is dispersed as an aerosol into the patients oral or nasal cavity. Such aerosols may be administered from a pump pack or from a pressurised pack containing a volatile propellant.

The therapeutically active compounds of formula I used in the method of the present invention may also be administered by continuous infusion either from an external source, for example by intravenous infusion or from a source of the compound placed within the body. Internal sources include implanted reservoirs containing the compound to be infused which is continuously released for example by osmosis and implants which may be (a) liquid such as an oily suspension of the compound to be infused for example in the form of a very sparingly water-soluble derivative such as a dodecanoate salt or a lipophilic ester or (b) solid in the form of an implanted support, for example of a synthetic resin or waxy material, for the compound to be infused. The support may be a single body containing all the compound or a series of several bodies each containing part of the compound to be delivered. The amount of active compound present in an internal source should be such that a therapeutically effective amount of the compound is delivered over a long period of time.

In some formulations it may be beneficial to use the compounds of the present invention in the form of particles of very small size, for example as obtained by fluid energy milling.

In the compositions of the present invention the active compound may, if desired, be associated with other compatible pharmacologically active ingredients.

The invention further provides the use of compounds of formula I in the manufacture of a medicament for treating gallstones, for example those gallstones which develop during weight loss or those associated with gall bladder disease related to an obese condition.

In another aspect, the invention further provides a pharmaceutical composition for treating gallstones, comprising a compound of formula I in conjunction with a pharmaceutically acceptable diluent or carrier.

Supersaturation of the bile and reduced motility of the gallbladder are thought to be underlying factors for gallstone formation. In addition, gallstones enhance the propensity to gallbladder inflammation, and acute and chronic cholecystitis is more common in the obese. Biliary colic and acute pancreatitis are other complications from gallstones. Obesity per se is associated with an increased risk of biliary disease. In addition, people who lose weight rapidly are at increased risk of developing gallstones during the period of weight loss. As the rate of weight loss with the compounds of formula I is gradual compared to many forms of therapy, the risk of developing gallbladder disease is reduced. Women who lose 4 to 10 kg have an increased risk of clinically relevant gallstone disease, and greater weight loss enhances this risk. Mobilization of cholesterol from adipose tissue stores is increased during weight loss and so the risk of supersaturation of bile is greater at this time than when weight is stable. Menopausal women are at particular risk because of an oestrogen-induced biliary secretion of cholesterol. The known ability of sibutramine to reduce cholesterol levels lowers the incidence of gallstones and related symptoms.

Monoamine reuptake inhibitors have been used to treat certain of the disorders described in the present invention.

However, these compounds are known to suffer from a number of disadvantages. Firstly such compounds are not effective in all patients. Secondly where the compounds are effective they may not provide a complete cure of the disorder. Thirdly, there are many undesirable side-effects known with this type of compound. Such side-effects include nausea, sexual dysfunction, light headedness, somnolence, sweating, tremor, dry mouth, asthenia, insomnia, diarrhoea, headache, vomiting, anxiety, drowsiness, dizziness, fever, rash or allergic reactions, arthralgia, myalgia, convulsions, hypomania and mania.

Sibutramine (Formula I, $R_1$=$CH_3$, $R_2$=$CH_3$) has a pharmacological profile which is unique amongst monoamine reuptake inhibitors. Through its pharmacologically active metabolites, (metabolite 1, $R_1$=H, $R_2$=$CH_3$ in Formula I and metabolite 2, $R_1$=H, $R_2$=H in Formula I) sibutramine inhibits the reuptake of all three monoamines differentiating it from serotonin (5-HT)-selective reuptake inhibitors, e.g. fluoxetine, noradenaline-selective reuptake inhibitors, e.g. desipramine, dopamine-selective reuptake inhibitors, e.g. bupropion, and serotonin-noradenaline reuptake inhibitors, e.g. venlafaxine (Table 1). It is this unique combination of pharmacological actions which renders sibutramine, and the other compounds of formula I, efficacious in the treatment of gallstones.

The assays below are performed in a similar manner to those described in WO98/41528.

TABLE

Comparison of the in vitro monoamine reuptake inhibition profiles of Examples 1 and 2, and various reference monoamine reuptake inhibitors in rat brain tissue

| | Ki (nM) | | |
|---|---|---|---|
| | [$^3$H]Noradenaline | [$^3$H]5-HT | [$^3$H]Dopamine |
| Example 1 | 3 | 18 | 24 |
| Example 2 | 5 | 26 | 31 |
| Bupropion | 2590 | 18312 | 409 |
| Desipramine | 2 | 200 | 4853 |
| Fluoxetine | 320 | 11 | 2025 |
| Venlafaxine | 196 | 26 | 2594 |

The results are the means of ≧3 separate determinations

Example 1 $R_1$=H, $R_2$=$CH_3$ in Formula I

Example 2 $R_1$=H, $R_2$=H in Formula I

The efficacy of compounds of formula I in treating gallstones is demonstrable through clinical trials in a relevant population set.

EXAMPLE 1

Sibutramine 10 mg orally once daily is administered in the morning during the time a patient is losing weight. The patient does not develop gallstones The invention has been described with reference to various specific embodiments. However, many variations and modifications may be made while remaining within the scope and spirit of the invention.

What is claimed is:

1. A method of treating gallstones comprising administering to a human in need thereof a therapeutically effective amount of a compound of formula 1,

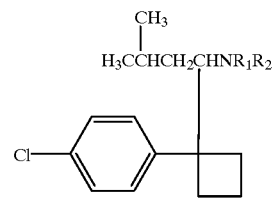

an enantiomer or a pharmaceutically acceptable salt thereof in which $R_1$ and $R_2$ are independently H or methyl, in conjunction with a pharmaceutically acceptable diluent or carrier.

2. The method as claimed in claim 1 in which the gallstones are developed as a result of losing weight.

3. The method as claimed in claim 1 or 2 wherein the compound of formula 1 is N,N-dimethyl-1-[1-(4-chlorophenyl)cyclobutyl]-3-methylbutylamine hydrochloride.

4. The method as claimed in claim 1 or 2 wherein the compound of formula 1 is N,N-dimethyl-1-[1-(4-chlorophenyl)cyclobutyl]-3-methylbutylarnine hydrochloride in the form of its monohydrate.

5. The method as claimed in claim 1 or 2 wherein the compound of formula 1 is (+)-N -{1-[1-(4-chlorophenyl)cyclobutyl]-3-methylbutyl}-N-methylamine.

6. The method as claimed in claim 1 or 2 wherein the compound of formula 1 is (−)-N -{1-[1-(4-chlorophenyl)cyclobutyl]-3-methylbutyl}-N-methylamine.

7. The method as claimed in claim 1 or 2 wherein the compound of formula 1 is (+)-1-[1-(4-chlorophenyl)cyclobutyl]-3-methylbutylamine.

8. The method as claimed in claim 1 or 2 wherein the compound of formula 1 is (−)-1-[1-(4-chlorophenyl)cyclobutyl]-3-methylbutylaamine.

9. The method as claimed in claim 1 or 2 wherein the compound of formula 1 is (+)-N-{1-[1-(4-chlorophenyl)cyclobutyl]-3-methylbutyl}-N-N-dimethylamine.

10. The method as claimed in claim 1 or 2 wherein the compound of formula I is (−)-N-{1-[1-(4-chlorophenyl)cyclobutyl]-3-methylbutyl}-N-N-dimethylamine.

11. The method as claimed in claim 1 or 2 wherein the compound of formula I is (±)-N-{1-[1-(4-chlorophenyl)cyclobutyl-3-methylbutyl}-N-methylamine.

12. The method as claimed in claim 1 or 2 wherein the compound of formula I is (±)-1-[1-(4-chlorophenyl)cyclobutyl]-3-methylbutylamine.

13. The method as claimed in claim 1 or 2 wherein the compound of formula I is (±)-N-{1-[1-(4-chlorophenyl)cyclobutyl]-3-methylbutyl}-N-N-dimethylamine.

\* \* \* \* \*